United States Patent [19]

Shealy et al.

[11] 4,396,623
[45] Aug. 2, 1983

[54] CARBOCYCLIC ANALOGS OF URACIL NUCLEOSIDES AS ANTIVIRAL AGENTS

[75] Inventors: Y. Fulmer Shealy; C. Allen O'Dell, both of Birmingham; William M. Shannon, Vestavia Hills, all of Ala.

[73] Assignee: Southern Research Institute, Birmingham, Ala.

[21] Appl. No.: 296,507

[22] Filed: Aug. 26, 1981

[51] Int. Cl.³ .................. A61K 31/505; C07D 239/10
[52] U.S. Cl. .................................. 424/251; 544/309; 544/311; 544/313; 544/314
[58] Field of Search ........................ 424/251; 544/311

[56]  References Cited

U.S. PATENT DOCUMENTS 4,177,348 12/1979 Shealy ................................ 544/317
4,232,154 11/1980 Shealy et al. ...................... 544/250

OTHER PUBLICATIONS

Murdock et al., J. Am. Chem. Soc., 84, (1962), pp. 3758–3764.
"Acid–Catalyzed Cyclization of Alkoxyacryloylureas to 2,4(1H,3H)pyrimidinediones", Shealy et al.; J. Heterocyclic Chem., 13 (1976), pp. 1015–1020, 1041–1047, 1353–1354.
"Carbocyclic Analogs of Thymine Nucleosides & Related 1-Substituted Thymines", Shealy et al; J. Heterocyclic Chem., 18 (1981), pp. 383–389.
"Carbocyclic Analogs of Cytosine Nucleosides", Shealy et al.; J. Heterocyclic Chem., 17 (1980), pp. 353–358.

Primary Examiner—Donald G. Daus
Assistant Examiner—W. A. Teoli
Attorney, Agent, or Firm—Roylance, Abrams, Berdo & Farley

[57]  ABSTRACT

There is provided a method for the treatment of viral infections by treating a host animal with a pharmaceutically effective amount of a carbocyclic analog of a nucleoside represented by Formula I:

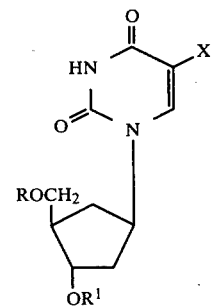

wherein X is chlorine, bromine, iodine, a lower alkyl group or an amino group of the formula —NHR² wherein R² is a lower alkyl group; and R and R' can be the same or different members selected from the group consisting of hydrogen, an alkanoyl group or an aroyl group.

16 Claims, No Drawings

CARBOCYCLIC ANALOGS OF URACIL NUCLEOSIDES AS ANTIVIRAL AGENTS

BACKGROUND OF THE INVENTION

1. Field of the Invention

This invention relates to analogs of uracil nucleosides in the treatment of viral infections. More particularly, this invention relates to carbocyclic analogs of uracil nucleosides in which the pentose moiety of the nucleosides is replaced by a cyclopentane ring in the treatment of viral infections. This invention also relates to certain novel carbocyclic analogs of uracil nucleosides.

2. Description of the Prior Art

Uracil nucleosides and the phosphate derivatives (nucleotides) of these nucleosides are obligatory components of the biosynthesis of nucleic acids, of certain interconversions of pyrimidine nucleosides and nucleotides, and of other essential biochemical events. Structural analogs of uracil nucleosides may interfere with enzymatic processes that require uracil nucleosides and nucleotides. Because of the essential involvement of uracil nucleosides and nucleotides in vital biochemical processes, interference with their functions may be manifested as important biological activity. The best known examples of clinically useful, antiviral nucleosides are 5-iodo-2'-deoxyuridine (IdUrd), a uracil nucleoside, and 9-β-D-arabinofuranosyladenine (Ara-A), a purine nucleoside. The antiviral activities, the clinical usefulness, and the disadvantages of IdUrd have been described in review articles such as "Recent Advances in Chemotherapy of Viral Diseases" by W. H. Prusoff in *Pharmacological Reviews*, volume 19, pages 209–250, 1967; "Purines and Pyrimidines" by F. M. Schabel, Jr., and J. A. Montgomery in *Chemotherapy of Virus Diseases, The International Encyclopedia of Pharmacology and Therapeutics*, volume 1, edited by D. J. Bauer, Pergamon Press, Oxford and New York, 1972; and "Antiviral Agents as Adjuncts in Cancer Chemotherapy" by W. M. Shannon and F. M. Schabel, Jr., in *Pharmacology and Therapeutics*, volume 11, pages 263–390, Pergamon Press, Oxford, Great Britain, 1980. Reviews of the antiviral activity of Ara-A include the latter review of Shannon and Schabel and "The Antiviral Activity of 9-β-D-arabinofuranosyladenine (Ara-A)" by F. M. Schabel, Jr., in *Chemotherapy*, volume 13, pages 321–338, 1968.

The term "carbocyclic analog of a nucleoside" designates a compound that has the same chemical structure as the nucleoside except that the oxygen atom of the furanose moiety of the nucleoside is replaced by a methylene group in the carbocyclic analog; or, differently expressed, in the carbocyclic analog a cyclopentane ring replaces the tetrahydrofuran ring of the analogous nucleoside. Such nucleoside analogs were designated carbocyclic analogs of nucleosides by Shealy and Clayton, *Journal of the American Chemical Society*, volume 88, pages 3885–3887, 1966. The natural nucleosides and many of their true nucleoside analogs are subject to the action of enzymes (phosphorylases and hydrolases) that cleave the nucleosides to the pentose and pyrimidine (or purine) moieties. The biological effects of such true nucleoside analogs may be lessened by the action of these degradative enzymes. In contrast, carbocyclic analogs of nucleosides do not possess the glycosidic bond present in the true nucleosides and, therefore, are not subject to the action of these degradative enzymes. They may also be more selective in their biological actions.

Carbocyclic analogs of uracil nucleosides in which X of Formula I, below, is hydrogen or methyl have been previously described by Shealy and O'Dell, *Journal of Heterocyclic Chemistry*, volume 13, pages 1015–1020, 1041–1047 and 1353–1354, 1976; and by Shealy, O'Dell and Thorpe, *Journal of Heterocyclic Chemistry*, volume 18, pages 383–389, 1981. Certain carbocyclic analogs of cytosine nucleosides have also been synthesized and described and their antiviral activity revealed by Shealy and O'Dell in U.S. Pat. No. 4,177,238, Dec. 4, 1979; U.S. Pat. No. 4,232,154, Nov. 4, 1980; and *Journal of Heterocyclic Chemistry*, volume 17, pages 353–358, 1980. The two U.S. patents disclose that analogs in which X of Formula I, below, is hydrogen, lower alkyl or halogen may be used as intermediates in the preparation of the cytosine nucleoside analogs. These patents also disclose that the hydroxyl groups on such compounds may be reacted with an acylating agent. Murdock et al in *Journal of the American Chemical Society*, volume 84, pages 3758–3764 (1962) claimed the formula of the carbocyclic analog of thymidine, i.e., the formula:

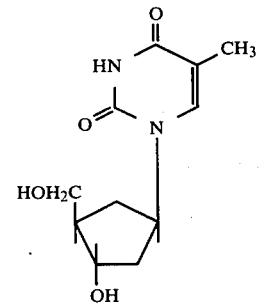

However, Shealy, O'Dell, and Thorpe, *Journal of Heterocyclic Chemistry*, Volume 18, pages 383–389, 1981, have shown that the compound claimed by Murdock is not the carbocylic analog of thymidine. None of these references disclose that the carbocyclic analogs of uracil nucleosides mentioned therein exhibit antiviral activity.

SUMMARY OF THE INVENTION

It has now been found that certain carbocyclic analogs of uracil nucleosides exhibit potent and advantageous activity against herpes viruses and other DNA viruses. Thus, in accordance with this invention, there is administered to a host animal, including man, afflicted with a viral infection a therapeutically effective amount of a carbocyclic analog of a nucleoside represented by Formula I

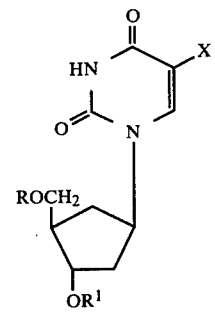

FORMULA I wherein X of chlorine, bromine, iodine, a lower alkyl group or an amino group of the formula —NHR$^2$ wherein R$^2$ is a lower alkyl group; and R and R$^1$ can be the same or different members selected from the group consisting of hydrogen, an alkanoyl group or an aroyl group. By "lower alkyl" is meant an alkyl group containing from one to six carbon atoms.

Compounds of Formula I are analogs of 5-substituted-2′-deoxyuridines in which the pentose moiety of the true (or conventional) nucleosides is replaced by an appropriately substituted cyclopentyl group; i.e., the tetrahydrofuran ring of the conventional nucleoside structure is replaced by a cyclopentane ring.

DETAILED DESCRIPTION OF THE INVENTION

Syntheses of the analogs of 5-substituted-2′-deoxyuridines may be carried out by beginning with the corresponding carbocyclic analogs of uracil nucleosides; i.e., compounds of Formula I wherein X is hydrogen. The synthesis of these precursor carbocyclic analogs was described by Shealy and O'Dell, *Journal of Heterocyclic Chemistry*, volume 13, pages 1015–1020, 1976. Alternatively, certain carbocyclic analogs of 5-substituted-2′-deoxyuridines may be synthesized from acyclic precursors according to the route described in the *Journal of Heterocyclic Chemistry*, volume 13, pages 1015–1020, 1976, except that the acyclic precursor bears a group positioned so as to become the desired 5-substituted-2′-deoxyuridine analog. For example, treatment of the carbocyclic analog of Formula I, wherein X, R and R$^1$ are each hydrogen, with bromine after the hydroxy groups have been acylated produces carbocyclic analogs of acylated 5-bromo-2′-deoxyuridines (Formula I, X=Br and R and R$^1$ are acyl groups). Hydrolysis of the acyl derivatives then produces the corresponding unacylated compound in which R and R$^1$ are hydrogen. The carbocyclic analogs (Formula I, X=I) of 5-iodo-2′-deoxyuridines may be synthesized by treating the precursor analogs (Formula I, X=H) with iodine in a mixture of chloroform and nitric acid. The compounds that are carbocyclic analogs of 5-(substituted-amino)-2′-deoxyuridines may be obtained by treating the appropriate 5-halouracil analogs (Formula I, X=Br, I, or Cl) with the appropriate amine.

The carbocyclic analogs of 5-substituted-2′-deoxyuridines of Formula I have pronounced antiviral activity and may be used in the treatment of various human and animal diseases caused by DNA viruses, such as herpes simplex viruses. For such uses, certain of these compounds offer distinct advantages over known and currently used antiviral nucleosides. Thus, certain of the carbocyclic analogs of 5-substituted-2′-deoxyuridine nucleosides are more active in inhibiting the replication of herpes simplex virus, type 1, than is, the clinically active drug 9-β-D-arabinofuranosyladenine (Ara-A). Furthermore, the carbocyclic analog of 5-iodo-2′-deoxyuridine (IdUrd) is active against experimental herpes simplex virus infection of the brain (encephalitis) as demonstrated by treatment of mice innoculated intracerebrally with herpes simplex virus, whereas IdUrd itself does not exhibit this type of antiviral activity (F. M. Schabel, Jr., *Chemotherapy*, volume 13, pages 321–328, 1968). The compounds of Formula I are administered in any physiologically acceptable method, e.g., topically or parenterally, in a therapeutically effective amount. Determination of optimum dosages is within the skill of the art.

The following examples illustrate the preparation of the compounds of Formula I. In these examples, the system of designating the orientation of substituents on the cyclopentane ring as α or β is that used by *Chemical Abstracts*, beginning with volume 76, in the Chemical Substance Index.

EXAMPLE 1

(±)-5-Bromo-1-[(1α,3β,4α)-3-hydroxy-4-(hydroxymethyl)cyclopentyl]-2,4(1H,3H)-pyrimidinedione Diacetate (Formula I, X=Br, R=R$^1$=CH$_3$CO—)

A mixture of acetic anhydride (11 ml) and (±)-1-[(1α,3β,4α)-3-hydroxy-4-(hydroxymethyl)cyclopentyl]-2,4(1H,3H)-pyrimidinedione (the carbocyclic analog of 2′-deoxyuridine) (1.00 gram) was boiled under reflux until the mixture became a homogeneous solution. The solution was cooled to room temperature and was stirred and maintained at 25° C. while a solution of bromine (826 mg.) in 1.1 ml. of acetic acid was added dropwise. The resulting solution was stirred at room temperature for 3 hours and then stored overnight at low temperature (about 5° C.) after additional reagent (206 mg. of bromine in 0.3 ml. of acetic acid) had been added. Volatile components were evaporated from the reaction solution under reduced pressure, and the crystalline residue was triturated with an ethanol-ether (1:1) mixture. The white solid was collected by filtration and dried under reduced pressure at 78° C.: weight, 1.605 grams (93% yield). Ultraviolet absorption data showed that this material was comparable to an analytically pure specimen. This compound may be purified, if desired, by recrystallizing it from ethanol: recovery, 84%; m.p. 164°–167° C.; ultraviolet absorption maxima in nanometers at 284 ($\epsilon$10,400) and 212 ($\epsilon$10,000) at pH 1, 282 ($\epsilon$9900) and 211 ($\epsilon$9600) at pH 7, and 280 ($\epsilon$7100) at pH 13; mass spectral peaks (M=molecular ion) at m/e 388 (M), 328 (M—CH$_3$COOH), 285 (M—CH$_3$CO—CH$_3$COOH), 268 (M—2CH$_3$COOH), 190 (5-bromouracilyl group+H); infrared spectrum (KBr disc, bands in the 1800–1400 cm$^{-1}$ region): 1740, 1720, 1700, 1680, 1620, 1500 (weak), 1460 (shoulder), 1450, 1430, 1380, 1360, 1320.

Analysis. Calcd. for C$_{14}$H$_{17}$BrN$_2$O$_6$: C, 43.20; H, 4.40; N, 7.20. Found: C, 43.06; H, 4.50; N, 7.24.

EXAMPLE 2

(±)-5-Bromo-1-[(1α,3β,4α)-3-hydroxy-4-(hydroxymethyl)cyclopentyl]-2,4(1H,3H)-pyrimidinedione (Formula I, X=Br, R=R$^1$=H), The Carbocyclic Analog of 5-Bromo-2′-deoxyuridine A solution of the diacetate (540 mg.) of Example 1 in 25 ml. of ammonia in methanol (10% ammonia) was stirred at room temperature for 72 hours and then concentrated to dryness under reduced pressure. The residue was dissolved in hot water (10 ml.), the solution was treated with activated carbon and filtered, and the filtrate (plus washings) was concentrated to about one-half of the original volume. After the concentrated solution had been stored at low temperature (about 5° C.), the white crystalline product was collected by filtration, washed sparingly with water, and dried in vacuo at 78° C.: yield 251 mg. (52%); m.p. 188°–193° C. After the filtrate had been concentrated and refrigerated, an additional quantity (60 mg., total yield=73.7%) of the desired carbocyclic analog was obtained in the same manner: m.p. 189°–194° C.; ultraviolet absorption maxima in nanometers at 284 ($\epsilon$10,000) and 212 ($\epsilon$9400)

at pH 1, 284 ($\epsilon$10,000) and 212 ($\epsilon$9600) at pH 7, and 280 ($\epsilon$7400) at pH 13; mass spectral peaks (M=molecular ion) at m/e 304 (M), 286 (M—$H_2O$), 274, 255 (M—$H_2O$—$CH_2OH$), 247, 217 (5-bromouracilyl group+$C_2H_4$), 191 (5-bromouracilyl group+2H), 190 (5-bromouracilyl group+H); infrared spectrum (KBr disc, bands in the 1800–1300 $cm^{-1}$ region): 1695, 1685, 1645, 1630 (shoulder), 1610, 1505 (weak), 1460, 1445, 1425, 1415 (shoulder), 1375, 1345, 1310.

Analysis. Calcd. for $C_{10}H_{13}BrN_2O_4$: C, 39.49; H, 4.29; N, 9.21. Found: C, 39.19; H, 4.29; N, 9.16.

EXAMPLE 3

($\pm$)-1-[(1$\alpha$,3$\beta$,4$\alpha$)-3-Hydroxy-4-(hydroxymethyl)cyclopentyl]-5-iodo-2,4(1$\underline{H}$,3$\underline{H}$)-pyrimidinedione (Formula I, X=I, R=$R^1$=H)

A solution of iodine (2.49 g.) in chloroform (13 ml.) was added to a solution of 2.175 g. of the carbocyclic analog (Formula I, X=R=$R^1$=H) of 2'-deoxyuridine in 1 N nitric acid (22 ml.), and the resulting mixture was heated under reflux for 2 hours and then stored overnight in a refrigerator (at about 5° C.). The chloroform layer was separated, and the water layer, which now contained a white solid, was again refrigerated. The white crystalline solid was collected by filtration, washed with cold water, and dried in vacuo at room temperature. The crude product (2.914 g.) was dissolved in hot water (75 ml.); the solution was filtered and then refrigerated; and the recrystallized product was collected by filtration, washed with cold water, and dried in vacuo at 78° C.: yield, 2.58 g. (76%); m.p. 197°–199° C.; ultraviolet absorption maxima (in nanometers) at 292 ($\epsilon$8800) and 217 ($\epsilon$10,900) at pH 1, 293 ($\epsilon$8700) and 217 ($\epsilon$11,000) at pH 7, 283 ($\epsilon$6400) at pH 13; mass spectral peaks (M=molecular ion) at m/e 352 (M), 334 (M—$H_2O$), 322, 303 (M—$H_2O$—$CH_2OH$), 295, 293, 265 (5-iodouracilyl group+$C_2H_4$), 260, 239 (5-iodouracilyl group+2H), 238 (5-iodouracilyl group+H), 225 (M—I); infrared spectrum (KBr disc, bands in the 1800–1300 $cm^{-1}$ region): 1690, 1640, 1600, 1505, 1460, 1420, 1400 (shoulder), 1345, 1305; proton nuclear magnetic resonance spectrum (100.1 MHz, dimethylsulfoxide-$D_6$ solution, $\delta$ in parts per million downfield from tetramethylsilane as internal standard): 1.2–1.7 and 1.7–2.3 (overlapping multiplets), 3.3–3.7 (multiplet), 4.0 (approximate center of multiplet), 4.5–4.7, 4.6–4.8, 4.6–5.2 (overlapping multiplets), 8.13 (singlet), 11.58 (broad singlet).

Analysis. Calcd. for $C_{10}H_{13}IN_2O_4$: C, 34.11, H, 3.72; N, 7.96. Found: C, 33.93; H, 3.77; N, 8.25.

EXAMPLE 4

($\pm$)-1-[(1$\alpha$,3$\beta$,4$\alpha$)-3-Hydroxy-4-(hydroxymethyl)cyclopentyl]-5-iodo-2,4(1$\underline{H}$,3$\underline{H}$)-pyrimidinedione Diacetate (Formula I, X=I, R=$R^1$=$CH_3CO$—)

A solution prepared from 450 mg. of the carbocyclic analog of 5-iodo-2'-deoxyuridine (Example 3), pyridine (20 ml.), and acetic anhydride (1 ml.) was stirred at room temperature for 3 days and then concentrated to a low volume. Cold water was added dropwise to the concentrated solution, and the resulting mixture, containing a gummy precipitate, was placed in a refrigerator to allow crystallization to occur. The crystalline precipitate was collected by filtration, washed well with cold water, and dried in vacuo at 78° C.: yield, 550 mg. (99%); m.p. 183°–186° C.; ultraviolet absorption maxima in nanometers at 293 ($\epsilon$8100) and 218 ($\epsilon$10,200) at pH 1, 292 ($\epsilon$8000) and 217 ($\epsilon$10,200) at pH 7, and 284 ($\epsilon$5800) at pH 13; mass spectral peaks (M=molecular ion) at m/e 436 (M), 376 (M—$CH_3COOH$), 316 (M—$2CH_3COOH$), 303 (M—$CH_3COOH$—$CH_2OCOCH_3$), 265 (5-iodouracilyl group+$C_2H_4$), 239 (5-iodouracilyl group+2H), 238 (5-iodouracilyl group+H); infrared spectrum (KBr disc, bands in the 1800–1300 $cm^{-1}$ region): 1725, 1690, 1665, 1610, 1590, 1515 (weak), 1445, 1435, 1420, 1375, 1355, 1345, 1320, 1305.

Analysis. Calcd. for $C_{14}H_{17}IN_2O_6$: C, 38.55; H, 3.93; N, 6.42. Found: C, 38.64; H, 4.05; N, 6.43.

EXAMPLE 5

($\pm$)-1-[(1$\alpha$,3$\beta$,4$\alpha$)-3-Hydroxy-4-(hydroxymethyl)cyclopentyl]-5-(methylamino)-2,4(1$\underline{H}$,3$\underline{H}$)-pyrimidinedione (Formula I, X=—$NHCH_3$, R=$R^1$=H)

A solution of the carbocyclic analog of 5-bromo-2'-deoxyuridine (Example 2, 175 mg.) in a 50% solution (30 ml.) of methylamine in methanol was heated at 90°–100° C. for 20 hours in a sealed stainless-steel bomb. The reaction solution was removed from the bomb, concentrated with a current of nitrogen to remove ammonia, and then concentrated in vacuo to a foam. A water (25 ml.) solution of the residue was chromatographed on a column of a cation resin (Amberlite CG-120, $H^+$ form). The resin column was washed thoroughly with water, and the 5-(methylamino)-2'-deoxyuridine analog was eluted from the column with 1 N aqueous ammonia. The basic eluate was concentrated to dryness in vacuo, ethanol (3 ml.) was added to the residue, the cloudy solution was filtered, and the clear filtrate was diluted carefully with ether (10 ml.). A white solid was collected by filtration, washed with ether, and dried in vacuo at 78° C.; weight, 37 mg. The filtrate was diluted with ether, and a second crop of white solid was then obtained in the same way; weight, 73 mg. (total yield as a hemihydrate=65.8%). The two crops of product were combined in hot ethanol, the solution was filtered, and the hot filtrate was diluted with ether. The white precipitate was collected by filtration, washed with ether, and dried in vacuo at 78° C.: recovery, 73%, ultraviolet absorption maxima in nanometers at 270 ($\epsilon$9400) at pH 1, 303 ($\epsilon$6400) and 236 ($\epsilon$6800) at pH 7, and 294 ($\epsilon$5800) and 230–240 (slight shoulder) at pH 13; mass spectral peaks (M=molecular ion) at m/e 256 (M+1), 255 (M), 237 (M—$H_2O$), 224 (M—$CH_2OH$), 206 (M—$H_2O$—$CH_2OH$), 167, 141 (5-(methylamino)uracilyl group+H); infrared spectrum (KBr disc, bands in the 1800–1300 $cm^{-1}$ region): 1700, 1660, 1635, 1595, 1585 (shoulder), 1510, 1500, 1475, 1465, 1455, 1440, 1425, 1395, 1370, 1320.

Analysis. Calcd. for $C_{11}H_{17}N_3O_4 \cdot 0.5H_2O$: C, 49.99; H, 6.87; N, 15.90. Found: C, 50.02; H, 6.71; N, 15.70.

EXAMPLE 6

($\pm$)-5-(Butylamino)-1-[(1$\alpha$,3$\beta$,4$\alpha$)-3-hydroxy-4-(hydroxymethyl)cyclopentyl]-2,4(1$\underline{H}$,3$\underline{H}$)-pyrimidinedione (Formula I, X=—$NHC_4H_9$, R=$R^1$=H)

A solution of the carbocyclic analog (Example 1, 400 mg.) of 5-bromo-2'-deoxyuridine diacetate in butylamine (25 ml.) was heated under reflux for 20 hours and then concentrated in vacuo to a gummy residue. Water (20 ml.) was added to the residue, and the aqueous mixture was extracted three times with 20-ml. portions of ether and then concentrated in vacuo to a colorless syrup (weight, 280 mg.). A water (50 ml.) solution of the residual syrup was chromatographed on a column of a cation resin as described in Example 5, and the basic eluate was concentrated in vacuo to a syrup that was dissolved in ethanol. The ethanol solution was filtered and concentrated to a colorless syrup; weight, 248 mg. (81% yield calculated as the free base form of the compound named in the title). The free base was converted to a sulfate salt as follows: 1 N sulfuric acid (1 ml.) was added to an ethanol (20 ml.) solution of the free base, the solution was concentrated to a low volume, the addition of ethanol and the concentration of the resulting solution were repeated several times to remove water, and ether was then added to the concentrated solution. A white solid, collected in two crops, was separated by filtration, washed with ether, and dried in vacuo at 78° C.: yield, 170 mg. (44% calculated as a sulfate, 1.25 hydrate); mass spectral peaks (M=molecular ion) at m/e 297 (M), 279 (M—$H_2O$), 254 (M—$C_3H_7$), 236 (M—$C_3H_7$—$H_2O$), 183 (5-butylamino)uracilyl group+H); infrared spectrum (KBr disc, bands in the 1800–1000 $cm^{-1}$ region): broad bands centered at 1690, 1585, 1495, 1465, 1440, 1395, 1380 (shoulder), 1310 (shoulder), 1280, 1210, 1165, 1115, 1040.

Analysis. Calcd. for $C_{14}H_{23}N_3O_4 \cdot 0.5H_2SO_4 \cdot 1.25H_2O$: C, 45.58; H, 6.97; N, 11.40. Found: C, 45.55; H, 6.82; N, 11.85.

EXAMPLE 7

Antiviral Activity of Carbocyclic Analogs of 5-Substituted-Uracil Nucleosides

Carbocyclic analogs of 5-substituted-2'-deoxyuridines were tested for antiviral activity against viruses that replicate in mammalian cells growing in cell culture. The results of these tests against herpes simplex virus, Type 1, growing in rabbit kidney cells are summarized in Table 1. The Virus Rating (VR) is a weighted measurement of antiviral activity determined by the method of Ehrlich et al, *Annals of the New York Academy of Science*, volume 130, pages 5–16, 1965. In tests carried out by this method, a VR of 0.5–0.9 indicates marginal to moderate antiviral activity and a VR equal to or greater than 1 indicates definite antiviral activity. The higher the value of VR, the greater is the antiviral activity. The $MIC_{50}$ (minimum inhibitory concentration, 50%) is the concentration of a test compound required for 50% inhibition of virus-induced cytopathogenic effect. The tests summarized in Table 1 show that carbocyclic analogs of 5-substituted-2'-deoxyuridines possess definite antiviral activity. Especially significant is the very high activity exhibited by the carbocyclic analog (Example 2) of 5-bromo-2'-deoxyuridine, the carbocyclic analog (Example 3) of 5-iodo-2'-deoxyuridine, the carbocyclic analog (Example 5) of 5-(methylamino)-2'-deoxy-uridine and the carbocyclic analog of thymidine. Furthermore, the compounds of Examples 2, 3, and 5 and the carbocyclic analog of thymidine showed high activity against Type 2 herpes simplex virus, values of VR being 1.5, 3.4, 1.2, and 3.2, respectively.

The advantage conferred by the presence of a substituent at position 5 of carbocyclic analogs of 2'-deoxyuridines is demonstrated by the fact that the parent compound, the carbocyclic analog of 2'-deoxyuridine (Formula I, X=H, R=$R^1$=H), is not active against herpes simplex virus (Table 1). However, not all carbocyclic analogs of 5-substituted-2'-deoxyuridines exhibit activity against herpes simplex virus. For example, the representative of Formula I wherein X is a primary amino group ($NH_2$) and R and $R^1$ are hydrogen was devoid of significant activity (VR=0.1) in the same type of test in which the compounds of Examples 5 and 6 (X=—$NHR^2$) are active (Table 1). Furthermore, in contrast to the high activity (Table 1) of the 5-halogen derivatives of Example 2 (Formula I, X=Br, R=$R^1$=H) and Example 3 (Formula I, X=I, R=$R^1$=H), another 5-halogen derivative, the carbocyclic analog of 5-fluoro-2'-deoxyuridine (Formula I, X=F, R=$R^1$=H), was not active (VR=0) in the same type of test against herpes simplex virus (Table 1).

Carbocyclic analogs of 5-substituted-2'-deoxyuridines may inhibit the replication of other DNA viruses. Thus, the carbocyclic analog (Example 3) of 5-iodo-2'-deoxyuridine is active against varicella-zoster virus replicating in human foreskin fibroblasts (Table 2). In a virus yield-reduction experiment, Example 3 produced a reduction in the titer of virus progeny $\geq 4.0$ $log_{10}$, and there were no observable virus-induced cytopathogenic effects at 10 days postinfection. The IdUrd analog (Example 3) was also active against murine leukemia virus, an RNA tumor virus. Replication of this virus in mouse embryo cells was completely inhibited at a drug concentration of 32 μg/ml.

TABLE 1

Antiviral Activity of Carbocyclic Analogs of 5-Substituted-2'-deoxyuridines

| Compound | Herpes Simplex Virus, Type 1 | |
|---|---|---|
| | Virus Rating (VR) | $MIC_{50}$ (mcg/ml) |
| Example 1 | 1.3 | 92 |
| Example 2 | 6.2 | 0.3 |
| Example 3 | 7.1 | 0.3 |
| Example 4 | 2.4 | 10 |
| Example 5 | 3.9 | 15 |
| Example 6 | 2.0 | 290 |
| Carbocyclic analog of thymidine | 5.4 | 0.8 |
| Formula I, X = F, R = $R^1$ = H | 0 | |
| Formula I, X = H, R = $R^1$ = H | 0 | |

TABLE 2

Inhibition of Varicella-Zoster Virus Replication In Human Foreskin Fibroblasts by Example 3

| | Drug Concentration, μM | Virus-Induced Cytopathogenic Effects at 10 Days Postinfection, % | Virus Yield $Log_{10}$ $CCID_{50}$/ml | $Log_{10}$ Reduction in Virus Titer |
|---|---|---|---|---|
| Virus Controls | 0 | 90 | $\geq 4.5$ | 0 |
| Example 3 | 320 | 0 | $\leq 0.5$ | $\geq 4.0$ |
| | 100 | 0 | $\leq 0.5$ | $\geq 4.0$ |
| | 32 | 0 | $\leq 0.5$ | $\geq 4.0$ |

Virus titers are expressed in terms of $log_{10}$ $CCID_{50}$ (cell culture infectious dose, 50%) units per ml., and the reduction in virus yield after drug treatment is expressed as a logarithm.

EXAMPLE 8

Comparisons of Antiviral Activity

The results of antiviral tests, performed as described in Example 7, of 5-iodo-2'-deoxyuridine (IdUrd), the carbocyclic analog (Example 3) of 5-iodo-2'-deoxyuridine, 9-β-D-arabinofuranosyladenine (Ara-A), the carbocyclic analog (Example 2) of 5-bromo-2'-deoxyuridine, the carbocyclic analog (Example 5) of 5-(methylamino)-2'-deoxyuridine and the carbocyclic analog of thymidine are summarized in Table 3. These results show that these carbocyclic analogs are more active than is Ara-A and that the carbocyclic analog of IdUrd is comparable in activity in these tests to IdUrd.

TABLE 3

Comparisons of Antiviral Activity

| Compound | Herpes Simplex Virus, Type 1 | |
|---|---|---|
| | Virus Rating (VR) | MIC$_{50}$ (mcg/ml) |
| 5-Iodo-2'-deoxyuridine | 6.9, 7.9 | 0.3 |
| Carbocyclic analog of 5-iodo-2'-deoxyuridine (Example 3) | 7.9, 7.4 | 0.1, 0.4 |
| 9-β-D-Arabinofuranosyladenine (Ara-A) | 2.7 (average) | 9.8 |
| Carbocyclic analog of 5'-bromo-2'-deoxyuridine (Example 2) | 6.2 | 0.3 |
| Carbocyclic analog of 5-(methylamino)-2'-deoxy-uridine (Example 5) | 4.2 | 10.0 |
| Carbocyclic analog of thymidine | 5.4 | 0.8 |

EXAMPLE 9

Activity of the Carbocyclic Analog of 5-Iodo-2'-deoxyuridine In Vivo

Mice were inoculated intracerebrally with ten times the LD$_{50}$ of herpes simplex virus. (The LD$_{50}$ is the amount of virus that would be lethal to 50% of the inoculated animals.) Some of these virus-infected mice were treated for seven days with the carbocyclic analog (Example 3) of IdUrd, and some of these virus-infected mice were not treated and served as a control group. The results of this experiment are summarized in Table 4. These results show that this compound is active against herpes encephalitis in experimental animals; in contrast, it has been shown that IdUrd itself is not active against herpes encephalitis in mice (F. M. Schabel, Jr., Chemotherapy, volume 13, pages 321–328, 1968).

TABLE 4

Activity of the Carbocyclic Analog of 5-Iodo-2'-deoxyuridine Against Intracerebral Herpes Simplex Virus in Mice

| Dose mg./kg. | % of Infected Mice that lived less than six days | % of Infected Mice that lived 10 days or longer | Median Survival Time in Days |
|---|---|---|---|
| 400 | 0 | 50 | 8.8 |
| 300 | 10 | 40 | 9.2 |
| 0 (control group) | 50 | 10 | 6.1 |

Although the invention has been described in considerable detail with specific reference to certain advantageous embodiments thereof, variations and modifications can be made without departing from the scope of the invention as described in the specification and defined in the appended claims.

We claim:

1. A process for the treatment of a host animal having a herpes virus infection which comprises administering to said host animal a therapeutically effective amount of a compound represented by the following formula:

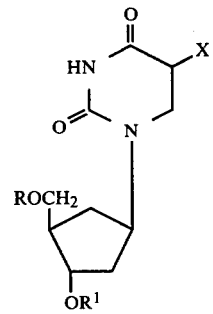

wherein X is bromine, iodine, methyl or an amino group of the formula —NHR$^2$ wherein R$^2$ is a C$_{1-4}$ lower alkyl group; and R and R$^1$ can be the same or different members selected from the group consisting of hydrogen or a C$_{1-6}$ alkanoyl group.

2. A process as defined in claim 1 wherein said virus infection is a herpes simplex virus infection.
3. A process as defined in claim 2 wherein X is Br.
4. A process as defined in claim 3 wherein each of R and R$^1$ is CH$_3$CO—.
5. A process as defined in claim 3 wherein each of R and R$^1$ is hydrogen.
6. A process as defined in claim 2 wherein X is I.
7. A process as defined in claim 6 wherein each of R and R$^1$ is hydrogen.
8. A process as defined in claim 6 wherein each of R and R$^1$ is CH$_3$CO—.
9. A process as defined in claim 2 wherein X is —NHCH$_3$ and each of R and R$^1$ is hydrogen.
10. A process as defined in claim 2 wherein X is —NHC$_4$H$_9$ and each of R and R$^1$ is hydrogen.
11. A process as defined in claim 2 wherein X is —CH$_3$ and each of R and R$^1$ is hydrogen.
12. A compound having the formula:

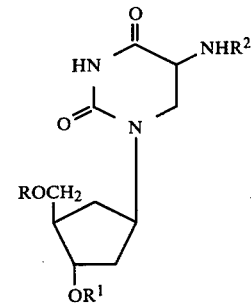

wherein R$^2$ is a C$_{1-4}$ lower alkyl group, and R and R$^1$ can be the same or different members selected from the group consisting of hydrogen or a C$_{1-6}$ alkanoyl group.

13. A compound as defined in claim 12 wherein X is —NHCH$_3$ and each of R and R$^1$ is hydrogen.
14. A compound as defined in claim 12 wherein X is —NHC$_4$H$_9$ and each of R and R$^1$ is hydrogen.
15. (±)-5-Bromo-1-[(1α,3β,4α)-3-hydroxy-4-(hydroxymethyl)cyclopentyl]-2,4(1H,3H)-pyrimidinedione diacetate.
16. (±)-1-[(1α,3β,4α)-3-Hydroxy-4-(hydroxymethyl)cyclopentyl]-5-iodo-2,4(1H,3H)-pyrimidinedione diacetate.

* * * * *

UNITED STATES PATENT AND TRADEMARK OFFICE
CERTIFICATE OF CORRECTION

PATENT NO. : 4,396,623
DATED : August 2, 1983
INVENTOR(S) : Y. Fulmer Shealy; C. Allen O'Dell; William M. Shannon It is certified that error appears in the above—identified patent and that said Letters Patent is hereby corrected as shown below:

Claim 1, that portion of the formula reading 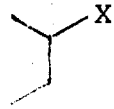

should read: 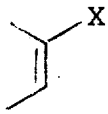

Claim 12, that portion of the formula reading 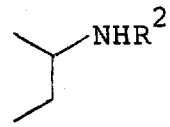

shoud read: 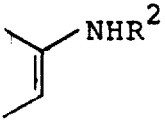

Signed and Sealed this

First Day of November 1983

[SEAL]

Attest:

GERALD J. MOSSINGHOFF

Attesting Officer

Commissioner of Patents and Trademarks